(12) United States Patent
Ipaye et al.

(10) Patent No.: US 11,154,483 B1
(45) Date of Patent: Oct. 26, 2021

(54) COMPOSITION TO SHORTEN DRYING TIME FOR HAIR

(71) Applicant: AMERICAN SPRAYTECH, L.L.C., North Branch, NJ (US)

(72) Inventors: Rasheedat Ipaye, East Orange, NJ (US); Aaysha Mustafa, North Brunswick, NJ (US); Manav A. Lalwani, Secaucus, NJ (US)

(73) Assignee: AMERICAN SPRAYTECH, L.L.C., North Branch, NJ (US)

( * ) Notice: Subject to any disclaimer, the term of this patent is extended or adjusted under 35 U.S.C. 154(b) by 0 days.

(21) Appl. No.: 16/414,000

(22) Filed: May 16, 2019

Related U.S. Application Data

(60) Provisional application No. 62/672,833, filed on May 17, 2018.

(51) Int. Cl.
| | |
|---|---|
| *A61K 8/73* | (2006.01) |
| *A61K 8/25* | (2006.01) |
| *A61K 8/26* | (2006.01) |
| *A61K 8/04* | (2006.01) |
| *A61K 8/37* | (2006.01) |
| *A61K 8/81* | (2006.01) |
| *A61K 8/34* | (2006.01) |
| *A61K 8/89* | (2006.01) |
| *A61Q 5/12* | (2006.01) |

(52) U.S. Cl.
CPC .............. *A61K 8/732* (2013.01); *A61K 8/046* (2013.01); *A61K 8/25* (2013.01); *A61K 8/26* (2013.01); *A61K 8/345* (2013.01); *A61K 8/37* (2013.01); *A61K 8/731* (2013.01); *A61K 8/817* (2013.01); *A61K 8/89* (2013.01); *A61Q 5/12* (2013.01)

(58) Field of Classification Search
None
See application file for complete search history.

(56) References Cited

U.S. PATENT DOCUMENTS

| | | |
|---|---|---|
| 4,091,079 A | 5/1978 | Vaughan |
| 5,378,670 A | 1/1995 | Kumar |
| 7,214,382 B2 | 5/2007 | Shefer et al. |
| 2009/0226381 A1 | 9/2009 | Maillefer et al. |
| 2012/0276035 A1 | 11/2012 | Lehman, Jr. |
| 2014/0137884 A1 | 5/2014 | Lehman |
| 2014/0140947 A1 | 5/2014 | Lehman |
| 2015/0374611 A1 | 12/2015 | Lehman |
| 2017/0043318 A1 | 2/2017 | Miller et al. |
| 2017/0281523 A1 | 10/2017 | Punyani et al. |

FOREIGN PATENT DOCUMENTS

| | | |
|---|---|---|
| WO | 9317661 A1 | 9/1993 |

OTHER PUBLICATIONS

Robin (IGK No More Blow Spray Lets You Air-Dry Hair Twice as Fast, available online at https://www.allure.com/story/igk-no-more-blow-high-speed-air-dry-spray, Apr. 24, 2018) (Year: 2018).*
IGK Hair No More Blow (available online at https://www.igkhair.com/collections/style-finish/products/no-more-blow-high-speed-air-dry-spray, accessed Oct. 15, 2020) (Year: 2020).*
Oh et al (Toxicol Res 30:297-304, 2014) (Year: 2014).*

* cited by examiner

*Primary Examiner* — Craig D Ricci
(74) *Attorney, Agent, or Firm* — Renner Kenner Greive Bobak Taylor and Weber; Tama L. Drenski

(57) ABSTRACT

Methods and compositions are provided that speed drying time for hair at room temperature. An aerosol hair drying aid composition includes a propellant portion and a liquid portion. The liquid portion includes at least one absorbent, at least one dispersing agent, at least one hair conditioning agent, and at least one non-aqueous solvent.

9 Claims, No Drawings

COMPOSITION TO SHORTEN DRYING TIME FOR HAIR

CROSS-REFERENCE TO RELATED APPLICATION

This application claims the benefits of U.S. Provisional Patent Application No. 62/672,833, filed May 17, 2018, which is incorporated herein by reference.

FIELD OF THE INVENTION

One or more embodiments of the present invention relate to compositions that reduce the amount of time needed for hair to dry.

BACKGROUND OF THE INVENTION

Many attempts have been made to reduce the drying time of hair. Blow dryers and other heat treatments can be used, although care must be taken to protect the hair from excessive heat. Even when blow-drying or other heat treatments are used, there is a desire to speed the drying process.

U.S. Patent Application Pub. No. 2014/0137884 teaches a composition and method for reducing the drying time of wet hair. The composition is a silicone-free, non-aqueous composition that includes a volatile hydrocarbon mixture of straight and branched chain paraffin compounds, an emollient, and a thermal protectant. The composition may also include one or more hair conditioning agents.

U.S. Patent Application Pub. No. 2014/0140947, which is also directed to a composition and method for reducing the drying time of wet hair, teaches a non-aqueous serum comprising a combination of about 55 to about 65 percent by weight of at least one volatile silicone compound, about 30 to about 40 percent by weight of at least one high molecular weight silicone elastomer, a thermo-protective agent, an emollient, and a conditioning agent.

U.S. Patent Application Pub. No. 2009/0226381 teaches a method and composition for improving the drying time of hair during styling, by impregnating it with a particular amino functional silicon derivative. The hair is made hydrophobic, which causes de-wetting.

U.S. Patent Application Pub. No. 2017/0281523 teaches a composition for providing a fast dry benefit on hair. The composition includes one or more moisture control materials that can penetrate inside the hair and coat the hair surface to result in less water on the hair surface and inside the hair.

Some current products that claim to decrease blow-dry time contain volatile silicones such as cyclopentasiloxane (D5). However, The European Commission Scientific Committee on Consumer Safety (SCCS) recently concluded that cyclopentasiloxane should not be used in hair styling formulations and other products that can give rise to lung exposure through inhalation. Other concerns of cyclopentasiloxane (D5) have been its effect on the environment.

There continues to exist a need for compositions and methods that reduce the time for drying hair.

SUMMARY OF THE INVENTION

The present invention provides methods and compositions that speed drying time for hair at room temperature. Advantageously, heat treatment is not necessary. One or more embodiments provide an aerosol hair drying aid composition that includes a propellant portion and a liquid portion. The liquid portion includes at least one absorbent, at least one dispersing agent, at least one hair conditioning agent, and at least one non-aqueous solvent.

DETAILED DESCRIPTION OF ILLUSTRATIVE EMBODIMENTS

In one or more embodiments, an aerosol hair drying aid composition is provided that includes a propellant portion and a liquid portion. The liquid portion includes at least one absorbent, at least one dispersing agent, at least one hair conditioning agent, and at least one non-aqueous solvent.

The aerosol hair drying aid composition may thus be described in terms of two portions: the propellant, and all other ingredients. All ingredients other than the propellant may be collectively referred to as the liquid portion, in spite of the fact that one or more of the individual ingredients may not be a liquid when in their normal state under standard conditions of room temperature (20-25° C.) and pressure (1 atm). The liquid portion, prior to being aerosolized, may be in the form of a solution, suspension, dispersion, or emulsion. The liquid portion may also be referred to as a drying aid concentrate. Accordingly, when discussing the effective amounts of components within the aerosol hair drying aid composition, the amounts may be stated based upon the drying aid concentrate, and may also be stated based upon the total aerosol hair drying aid composition, i.e. including the propellant.

In one or more embodiments, the aerosol hair drying aid composition includes a propellant portion. The propellant portion includes at least one propellant. Propellants may be used individually or blended together. Advantageously, the selection of a propellant or blend of propellants may be used to achieve a particular spray pattern, control particle size, conform to government regulations, or for cost considerations.

Propellants may be selected from the group consisting of hydrocarbons, hydrofluorocarbons, ethers, and combinations thereof. Examples of hydrocarbon propellants include pentane, n-butane (A-17), isobutane (A-31), and propane (A-108), and mixtures thereof. Examples of hydrocarbon blends include mixtures of propane and butane (A-46). Examples of hydrofluorocarbon propellants include 1,1,1,2-tetrafluoroethane (134a), 2,3,3,3-tetrafluoropropene (HFO-1234yf), 1,3,3,3-tetrafluoropropene (HFO-1234ze), and 1,1-difluoroethane (152a). An example of an ether propellant includes dimethyl ether. In one or more embodiments, the aerosol hair drying aid composition includes one or more hydrocarbon propellants and one or more hydrofluorocarbons. In one or more embodiments, the propellant includes butane and propane.

In one or more embodiments, the propellant includes from about 15 to about 40 wt. % propane, and in other embodiments, from about 20 to about 35 wt. % propane, based upon the total weight of propellant. In these or other embodiments, the propellant includes from about 50 to about 80 wt. % butane, in other embodiments, from about 60 to about 75 wt. % butane, based upon the total weight of propellant.

In one or more embodiments, the aerosol hair drying aid composition includes at least 2 wt. % propellant, in other embodiments, at least 5 wt. %, in other embodiments, at least 10 wt. %, in other embodiments, at least 15 wt. %, in other embodiments, at least 20 wt. %, in other embodiments, at least 25 wt. %, in other embodiments, at least 30 wt. %, in other embodiments, at least 35 wt. %, in other embodiments, at least 40 wt. %, in other embodiments, at least 45 wt. %, in other embodiments, at least 50 wt. %, in other embodiments, at least 55 wt. %, in other embodiments, at least 60 wt. %, in other embodiments, at least 65 wt. %, in other embodiments, at least 70 wt. %, in other embodiments, at least 75 wt. %, in other embodiments, at least 80 wt. %, in other embodiments, at least 85 wt. %, and in other embodiments, at least 90 wt. % propellant, based upon the total weight of the aerosol hair drying aid composition.

In one or more embodiments the total amount of propellant is from about 2 to about 99 wt. %, in other embodiments from about 4 to about 97 wt. %, and in other embodiments from about 5 to about 96 wt. %, based upon the total weight of the aerosol hair drying aid composition.

In one or more embodiments, the drying aid concentrate includes at least one absorbent, at least one dispersing agent, at least one hair conditioning agent, and at least one non-aqueous solvent.

In one or more embodiments, the absorbent may function as a moisture absorber and/or an oil absorber. Examples of absorbents include starches, silica, kaolin, cellulose, chalk, talc, fullers earth, alumina silicates, including zeolites, diatomaceous earths, and the like, and combinations thereof.

In one or more embodiments, the absorbent includes one or more starches. Non-limiting examples of starch materials include cornstarch, potato starch, tapioca starch, rice starch, wheat starch, and cassaya starch. A starch material may be modified or unmodified. A modified starch material is a starch which has been derivatized or altered by processes known to those of ordinary skill in the art, such as esterification, etherification, oxidation, acid hydrolysis, crosslinking, or enzyme conversion. Non-limiting examples of modified starch materials include aluminum starch octenylsuccinate, sodium starch octenylsuccinate, calcium starch octenylsuccinate, distarch phosphate, hydroxyethyl starch phosphate, hydroxypropyl starch phosphate, sodium carboxymethyl starch, and sodium starch glycolate.

Suitable starches include corn starch, potato starch, tapioca starch, rice starch, wheat starch and cassava starch. In one or more embodiments, the absorbent includes corn starch.

In one or more embodiments, the absorbent includes one or more zeolites. Zeolites are further described in International Patent Application Pub. No. WO 93/17661 A1, U.S. Pat. Nos. 4,091,079, 5,378,670, and U.S. Patent Application Pub. No. 2017/0043318 A1, all of which are incorporated by reference herein. In one or more embodiments, the zeolite is a micronized, highly porous, crystalline aluminosilicate (also called molecular sieve), available under the trade name SYLOSIV® Molecular Sieve Powder from W.R. Grace & Co.

In one or more embodiments, two or more absorbents are present in the drying aid concentrate. In one or more embodiments, the absorbents include one or more starches and one or more zeolites.

In one or more embodiments, the amount of total absorbing agent is from about 0.1 wt. % to about 75 wt. %, in other embodiments, from about 0.5 wt. % to about 60 wt. %, in other embodiments, from about 1 wt. % to about 50 wt. %, and in other embodiments, from about 2 wt. % to about 40 wt. %, based upon the total weight of the drying aid concentrate.

In one or more embodiments, the amount of total absorbing agent is from about 0.005 wt. % to about 70 wt. %, in other embodiments, from about 0.02 wt. % to about 55 wt. %, in other embodiments, from about 0.05 wt. % to about 45 wt. %, and in other embodiments, from about 0.1 wt. % to about 30 wt. %, based upon the total weight of the aerosol hair drying aid composition, including propellant.

In one or more embodiments, the aerosol hair drying aid composition includes up to 60 wt. % absorbing agent, in other embodiments, up to 50 wt. %, in other embodiments, up to 40 wt. %, in other embodiments, up to 30 wt. %, in other embodiments, up to 25 wt. %, in other embodiments, up to 20 wt. %, in other embodiments, up to 10 wt. %, in other embodiments, up to 5 wt. %, in other embodiments, up to 3 wt. % absorbing agent, based upon the total weight of the aerosol hair drying aid composition.

In one or more embodiments, the amount of total starch is from about 0.1 wt. % to about 75 wt. %, in other embodiments, from about 0.5 wt. % to about 60 wt. %, in other embodiments, from about 1 wt. % to about 50 wt. %, and in other embodiments, from about 2 wt. % to about 40 wt. %, based upon the total weight of the drying aid concentrate.

In one or more embodiments, the amount of starch is from about 0.005 wt. % to about 70 wt. %, in other embodiments, from about 0.02 wt. % to about 55 wt. %, in other embodiments, from about 0.05 wt. % to about 45 wt. %, and in other embodiments, from about 0.1 wt. % to about 30 wt. %, based upon the total weight of the aerosol hair drying aid composition, including propellant.

In one or more embodiments, the aerosol hair drying aid composition includes up to 60 wt. % starch, in other embodiments, up to 50 wt. %, in other embodiments, up to 40 wt. %, in other embodiments, up to 30 wt. %, in other embodiments, up to 25 wt. %, in other embodiments, up to 20 wt. %, in other embodiments, up to 10 wt. %, in other embodiments, up to 5 wt. %, in other embodiments, up to 3 wt. % starch, based upon the total weight of the aerosol hair drying aid composition.

In one or more embodiments, the aerosol hair drying aid composition includes up to 60 wt. % zeolite, in other embodiments, up to 50 wt. %, in other embodiments, up to 40 wt. %, in other embodiments, up to 30 wt. %, in other embodiments, up to 25 wt. %, in other embodiments, up to 20 wt. %, in other embodiments, up to 10 wt. %, in other embodiments, up to 5 wt. %, in other embodiments, up to 3 wt. % zeolite, based upon the total weight of the aerosol hair drying aid composition.

In one or more embodiments, the drying aid concentrate includes one or more dispersing agents. Examples of dispersing agents include organic modified clay mineral, such as disteardimonium hectorite.

In one or more embodiments, the concentrate includes at least about 0.05 wt. % of dispersing agents, in other embodiments, at least about 0.1 wt. %, in other embodiments, at least about 0.2 wt. %, based upon the total weight of the concentrate.

In one or more embodiments, the concentrate includes from about 0.05 to about 12 wt. % of dispersing agents, in other embodiments, from about 0.1 to about 10 wt. %, in other embodiments, from about 0.2 to about 5 wt. % of dispersing agents, based upon the total weight of the concentrate.

In one or more embodiments, where the hair drying aid composition is provided as an aerosol, the percentage weight of the dispersing agent(s) may be from about 0.0025 to about 10 wt. %, in other embodiments, from about 0.005 to about 8 wt. %, and in other embodiments, from about 0.01 to about 5 wt. %, based upon the total weight of the aerosol hair drying aid composition.

The drying aid concentrate of the present invention may contain one or more hair conditioning agents. In one or more embodiments, the hair conditioning agent may provide hydration, lubrication, and/or occlusion to the hair.

Examples include humectants and other moisturizing ingredients, and emollients. Emollients may act to form a smooth, even film on the surface of the hair, and/or to soften the hair, without leaving an unpleasant, sticky, or greasy texture. In one or more embodiments, the hair conditioning agents are silicon-free.

Examples of emollients for hair includes hydrophobic oils, fatty alcohols, fruit and vegetable-derived oils and butters, proteins and hydrolyzed proteins, mineral oil, petrolatum, and polyquaterniums. In one or more embodiments, the emollient may be selected from fatty acid esters and esters of alkoxylated aromatic alcohol and fatty carboxylic acids, and combinations thereof. Esters of alkoxylated aromatic alcohol and fatty carboxylic acids are further described in U.S. Pat. No. 6,987,195, which is incorporated herein by reference. Examples of conditioning agents include diisopropyl adipate, PPG-3 benzyl ether myristate, polyquaternium-59, butylene glycol, and hydrolyzed pea protein PG-propyl silantriol.

In one or more embodiments, the amount of total hair conditioning agent(s) is from about 0.01 to about 25 wt. %, in other embodiments, from about 0.05 to about 20 wt. %, and in other embodiments, from about 0.1 to about 15 wt. %, based upon the total weight of the drying aid concentrate.

In one or more embodiments, the aerosol hair drying aid composition includes up to 22 wt. %, in other embodiments, up to 20 wt. %, in other embodiments, up to 18 wt. %, in other embodiments, up to 16 wt. %, and in other embodiments, up to 15 wt. %, based upon the total weight of the aerosol hair drying aid composition.

In one or more embodiments, the amount of total hair conditioning agent(s) is from about 0.0005 to about 20 wt. %, in other embodiments, from about 0.0025 to about 15 wt. %, and in other embodiments, from about 0.005 to about 10 wt. %, based upon the total weight of the aerosol hair drying aid composition, including propellant.

In one or more embodiments, the drying aid concentrate includes one or more non-aqueous solvents. In one or more embodiments, the non-aqueous solvent may be selected from the group consisting of silicon-containing solvents, alcohol solvents and polyol solvents, hydrocarbon solvents, esters, mineral spirits, and combinations thereof.

Examples of alcohol solvents include $C_{1-9}$ alcohols. In one or more embodiments, the alcohol solvent is selected from the group consisting of methanol, ethanol, propanol, butanol, pentanol, hexanol, heptanol, octanol, decanol, and isomers and combinations thereof. Examples of polyol solvents include sorbitol, and alkylene glycols such as butylene glycol, propylene glycol, propylene glycol, and dipropylene glycol. Examples of silicon-containing solvents include hexamethyl disiloxane, which is sometimes referred to as bis(trimethylsilyl)oxide, and sometimes referred to by the INCI name of Disiloxane. In one or more embodiments, the non-aqueous solvent may be selected from the group consisting of alcohol solvents and polyol solvents, hydrocarbon solvents, esters, mineral spirits, and combinations thereof.

In one or more embodiments, the non-aqueous solvent is selected from the group consisting of $C_{1-9}$ monoalcohol solvents, and combinations thereof. In one or more embodiments, the drying aid concentrate further comprises one or more silicon-containing solvents.

In one or more embodiments, the drying aid concentrate includes a total of at least about 20 wt. % of non-aqueous solvent, in other embodiments, at least about 40 wt. %, in other embodiments, at least about 50 wt. %, in other embodiments, at least about 60 wt. %, based upon the total weight of the drying aid concentrate.

In one or more embodiments, the drying aid concentrate includes up to 90 wt. % of non-aqueous solvent, in other embodiments, up to 85 wt. %, in other embodiments, up to 80 wt. %, in other embodiments, up to 75 wt. %, in other embodiments, up to 70 wt. %, and in other embodiments, up to 65 wt. % non-aqueous solvent, based upon the total weight of the drying aid concentrate.

In one or more embodiments the total amount of non-aqueous solvent in the drying aid concentrate is from about 20 wt. % to about 90 wt. %, in other embodiments, from about 40 wt. % to about 85 wt. %, and in other embodiments, from about 50 wt. % to about 80 wt. %, based upon the total weight of the drying aid concentrate.

In one or more embodiments, the aerosol hair drying aid composition includes a total of at least about 1 wt. % of non-aqueous solvent, in other embodiments, at least about 1.5 wt. %, in other embodiments, at least about 2 wt. %, in other embodiments, at least about 2.5 wt. % non-aqueous solvent, based upon the total weight of the aerosol hair drying aid composition.

In one or more embodiments, the aerosol hair drying aid composition includes up to 60 wt. % of non-aqueous solvent, in other embodiments, up to 55 wt. %, in other embodiments, up to 50 wt. %, in other embodiments, up to 45 wt. %, in other embodiments, up to 40 wt. %, and in other embodiments, up to 35 wt. %, in other embodiments, up to 30 wt. %, in other embodiments, up to 25 wt. %, in other embodiments, up to 20 wt. %, and in other embodiments, up to 15 wt. %, in other embodiments, up to 10 wt. %, and in other embodiments, up to 5 wt. %, non-aqueous solvent, based upon the total weight of the aerosol hair drying aid composition.

In one or more embodiments the amount of non-aqueous solvent in the aerosol hair drying aid composition is from about 1 wt. % to about 85 wt. %, in other embodiments, from about 2 wt. % to about 80 wt. %, and in other embodiments, from about 2.5 wt. % to about 75 wt. %, based upon the total weight of the aerosol hair drying aid composition.

In one or more embodiments, the drying aid concentrate includes a total of at least about 20 wt. % of $C_{1-9}$ monoalcohol, in other embodiments, at least about 40 wt. %, in other embodiments, at least about 50 wt. %, in other embodiments, at least about 60 wt. %, based upon the total weight of the drying aid concentrate.

In one or more embodiments, the drying aid concentrate includes up to 90 wt. % of $C_{1-9}$ monoalcohol, in other embodiments, up to 85 wt. %, in other embodiments, up to 80 wt. %, in other embodiments, up to 75 wt. %, in other embodiments, up to 70 wt. %, and in other embodiments, up to 65 wt. % $C_{1-9}$ monoalcohol, based upon the total weight of the drying aid concentrate.

In one or more embodiments the total amount of $C_{1-9}$ monoalcohol in the drying aid concentrate is from about 20 wt. % to about 90 wt. %, in other embodiments, from about 40 wt. % to about 85 wt. %, and in other embodiments, from about 50 wt. % to about 80 wt. %, based upon the total weight of the drying aid concentrate.

In one or more embodiments, the aerosol hair drying aid composition includes a total of at least about 1 wt. % of $C_{1-9}$ monoalcohol, in other embodiments, at least about 1.5 wt. %, in other embodiments, at least about 2 wt. %, in other embodiments, at least about 2.5 wt. % $C_{1-9}$ monoalcohol, based upon the total weight of the aerosol hair drying aid composition.

In one or more embodiments, the aerosol hair drying aid composition includes up to 60 wt. % of $C_{1-9}$ monoalcohol, in other embodiments, up to 55 wt. %, in other embodiments, up to 50 wt. %, in other embodiments, up to 45 wt. %, in other embodiments, up to 40 wt. %, and in other embodiments, up to 35 wt. %, in other embodiments, up to 30 wt. %, in other embodiments, up to 25 wt. %, in other embodiments, up to 20 wt. %, and in other embodiments, up to 15 wt. %, in other embodiments, up to 10 wt. %, and in other embodiments, up to 5 wt. %, $C_{1-9}$ monoalcohol, based upon the total weight of the aerosol hair drying aid composition.

In one or more embodiments the amount of $C_{1-9}$ monoalcohol in the aerosol hair drying aid composition is from about 1 wt. % to about 85 wt. %, in other embodiments, from about 2 wt. % to about 80 wt. %, and in other embodiments, from about 2.5 wt. % to about 75 wt. %, based upon the total weight of the aerosol hair drying aid composition.

Advantageously, the amount of silicon-containing solvents may be limited, particularly volatile silicone compounds. Volatile silicone compounds generally have an atmospheric pressure boiling point of less than about 220° C., or between about 50° C. and about 220° C., and contain between about 3 and about 7 silicon atoms. Examples of volatile silicone compounds include polydimethylsiloxanes (e.g., having a viscosity less than about 5 cSt at 25° C.), cyclomethicone, cyclohexane siloxane, decamethyltetrasiloxane, octamethyltrisiloxane, decamethylpentasiloxane, cyclopentasiloxane, decamethylcyclopentasiloxane, octamethylcyclotetrasiloxane, trimethylsilylamodimethicone, phenyl trimethicone, hexamethyidisiloxane, dimethylsiloxane/methylalkylsiloxane, or combinations thereof.

In one or more embodiments the drying aid concentrate includes less than about 20 wt. % of silicon-containing solvents, in other embodiments, less than about 15 wt. %, in other embodiments, less than about 10 wt. %, in other embodiments, less than about 5 wt. %, in other embodiments, less than about 1 wt. %, based upon the total weight of the drying aid concentrate.

In embodiments where the aerosol hair drying aid composition is provided as an aerosol, the total percentage weight of silicon-containing solvents may be less than about 1 wt. %, in other embodiments, less than about 0.8 wt. %, in other embodiments, less than about 0.5 wt. %, in other embodiments, less than about 5 wt. %, in other embodiments, less than about 0.2 wt. %, based upon the total weight of the aerosol hair drying aid composition.

In some embodiments, the aerosol hair drying aid composition may comprise at one or more additional optional ingredients. Non-limiting examples of additional optional components include sensory ingredients such as warming agents, anti-caking agents, viscosity modifiers, antioxidants, essential oils, perfumes, waxes, fillers, hair-fixative polymers, deodorizing agents, pediculicides, anti-dandruff agents, cosmetic and/or dermatological active agents including vitamins (e.g., vitamin B complexes (e.g., including thiamine, nicotinic acid, biotin, pantothenic acid, choline, riboflavin, vitamin B6, vitamin B12, pyridoxine, inositol, carnitine), vitamins A, C, D, E, K and their derivatives (e.g., vitamin A palmitate) or pro-vitamins), essential fatty acids, sunscreens, herb and/or plant extracts (e.g., aloe), dispersing or suspending agents (e.g., silica); pharmaceutically active agents (e.g., poly(2-hydroxystearic acid); anti-static agents (e.g., tricetyl methyl ammonium chloride); pearlescent aids (e.g., such as coated mica, ethylene glycol distearate), opacifiers (e.g., tin), odor neutralizers, sequestering agents, and combinations thereof.

In one or more embodiments, the aerosol hair drying aid composition may include an anti-caking agent. Examples of anti-caking agents include polyuria powders, such as Methoxy PEG-17/Methoxy PEG-11/HDI Isocyanurate Trimer Crosspolymer, available from Covestro.

In one or more embodiments the total amount of anti-caking agent in the drying aid concentrate is from about 0.1 wt. % to about 20 wt. %, in other embodiments, from about 0.5 wt. % to about 15 wt. %, and in other embodiments, from about 1 wt. % to about 10 wt. %, based upon the total weight of the drying aid concentrate.

In one or more embodiments the amount of anti-caking agent in the aerosol hair drying aid composition is from about 0.005 wt. % to about 1 wt. %, in other embodiments, from about 0.01 wt. % to about 0.8 wt. %, and in other embodiments, from about 0.05 wt. % to about 0.6 wt. %, based upon the total weight of the aerosol hair drying aid composition.

In one or more embodiments, the aerosol hair drying aid composition may include a warming agent. In one or more embodiments, the aerosol drying aid composition exhibits self-heating action when exposed to water, such as when the composition is applied to wet hair. Examples of warming agents include PEG-4 (and) PEG-8 (and) PVP, available from Innospec Performance Chemicals under the tradename XO-THERM-SP. Examples of warming agents also include menthol and menthol derivatives, such as Menthol (and) Menthyl Lactate. Examples of warming agents also include and Vanilyl Butyl Ether. Combinations of warming agents may be employed. Warming agents are further described in U.S. Pat. No. 7,214,382, which is hereby incorporated by reference.

In one or more embodiments, the total amount of warming agent in the drying aid concentrate is from about 0.01% to about 10 wt. %, in other embodiments, from about 0.05% to about 5 wt. %, in other embodiments, from about 0.1% to about 3 wt. %, based upon the total weight of the drying aid concentrate.

In one or more embodiments the amount of warming agent in the aerosol hair drying aid composition is from about 0.0005 to about 1 wt. %, in other embodiments, from about 0.001 to about 0.5 wt. %, in other embodiments, from about 0.005 to about 0.2 wt. %, based upon the total weight of the aerosol hair drying aid composition.

The identity and amount of each optional ingredient is not particularly limited, so long as they do not deleteriously affect the performance of the semi-permanent hair colorant composition. Generally, one of ordinary skill in the art can determine the effective amount of each optional ingredient. Typically, the effective amount of an optional ingredient will be from about 0.01% to about 10 wt. %, in other embodiments, from about 0.05% to about 5 wt. %, in other embodiments, from about 0.1% to about 3 wt. %, in other embodiments, from about 0.01% to about 1 wt. %, based upon the total weight of the drying aid concentrate.

Typically, the effective amount of an optional ingredient will be from about 0.0005 to about 9 wt. %, in other embodiments, from about 0.001 to about 7 wt. %, in other embodiments, from about 0.01 to about 3 wt. %, in other embodiments, from about 0.001% to about 7 wt. %, in other embodiments, from about 0.01 to about 5%, based upon the total weight of the aerosol hair drying aid composition.

The drying aid concentrate may be prepared by any suitable method. In one or more embodiments, solid ingredients may be dissolved or dispersed in solvent with mixing, and then other ingredients are added.

The aerosol hair drying aid composition may be prepared using any suitable technique, as will be known to those of ordinary skill in the art. In some cases, the aerosol hair drying aid composition may be prepared by mixing an appropriate amount of a liquefied gaseous propellant and a drying aid concentrate under pressure, followed by packing the mixture in an aerosol container. In other cases, an aerosol container may be loaded with the drying aid concentrate, followed by pressurizing the container with a propellant and sealing the container.

The aerosol hair drying aid compositions of the present invention may be dispensed using aerosol powder dispensers. In one or more embodiments, the aerosol powder dispenser includes powder valves with a non-mechanical breakup actuator. Examples of suitable dispenser systems include those having a Lindal™ stem valve for antiperspirant and powder products, such as male valve CA39F, and a Lindal™ over-cup actuator for antiperspirant and powder products, such as Carla actuators for male valves. The aerosol powder spray compositions may be sprayed or otherwise applied directly onto skin. The liquid spray is clear and colorless when dispensed onto the skin, and dries quickly.

An aerosol hair drying aid composition is provided that exhibits reduced drying time. Blow dryers and heat treatments are not necessary.

The present invention further provides a method for reducing drying time of hair, the method comprising the steps of applying to the hair and aerosol hair drying aid composition that includes a propellant portion and a liquid portion, the liquid portion comprising at least one absorbent; at least one dispersing agent; at least one hair conditioning agent.

In order to demonstrate the practice of the present invention, the following examples have been prepared and tested. The examples should not, however, be viewed as limiting the scope of the invention. The claims will serve to define the invention.

EXPERIMENTAL

Sample 1—A drying aid concentrate sample was prepared according to the method described above. Sample 1 was a concentrate composition according to the present invention. Sample 1 included at least one absorbent, at least one dispersing agent, at least one hair conditioning agent, and at least one non-aqueous solvent. More specifically, Sample 1 is summarized in the table below.

| INCI NAME | TRADE NAME | CONC. Wt. % |
| --- | --- | --- |
| Butane/Propane | AB-46 | 85 |
| Tetrafluoropropene | Solstice 1234z | 10 |
| Ethanol | SDA Alcohol 40 B | 2.995 |
| Disiloxane | Jeesilc PDS 0.65 | 0.4 |
| Diisopropyl Adipate | Hallstar DIPA | 0.015 |
| PPG-3 Benzyl Ether Myristate | Crodamol STS | 0.175 |
| Disteardimonium Hectorite | Bentone 38 VCG | 0.015 |
| Methoxy PEG-17/Methoxy PEG-11/HDI Isocyanurate Trimer Cross Polymer | Baycusan C 1005 | 0.4 |
| Zea Mays (Corn) Starch | Purity 21C Pure | 1 |
| TOTAL | | 100 |

To prepare the concentrate, the non-aqueous solvent(s) was mixed with the skin conditioning agents and/or other ingredients that are normally solids at standard conditions of room temperature and pressure until a clear solution is obtained, i.e. the skin conditioning agents are dissolved in the solvent. Other liquid ingredients were added and mixed until fully dissolved or homogenized to form a homogeneous mixture. In a high shear mixer, the homogeneous mixture was combined with the dispersing agent and absorbing agent(s) to form the concentrate.

Aerosolized Samples were prepared as follows: an aerosol container was loaded with a Sample concentrate, then the container was pressurized with a propellant and sealed.

The samples were tested at room temperature and pressure as follows: Swatches of human hair were weighed to obtain an initial weight for each swatch. The swatches were run under water until completely wet. The samples were towel-dried. Each swatch was then weighed again to obtain a wet weight for each swatch. Each Sample was applied to a swatch, by spraying 5-10 seconds, or until there was a good coverage of Sample on the hair. One swatch was left untreated, as a control. Each Sample was immediately weighed again to obtain a treated weight for each swatch. Thereafter, each Sample was weighed every 30 seconds for 10 minutes. Then, each Sample was weighed every 5 minutes, until the weight of the Sample was equal to the initial weight plus the weight of Sample that was applied to the swatch (obtained by subtracting the wet weight from the treated weight).

The control swatch was 35% dry after about 10 minutes. In contrast, the swatches that were treated with the hair drying aid compositions of the present invention were at least 70% dry after about 10 minutes. In some embodiments, swatches that were treated with the hair drying aid compositions of the present invention were at least 90% dry after about 10 minutes. The swatch that was treated with Sample 1 was 90% dry after about 10 minutes.

Various modifications and alterations that do not depart from the scope and spirit of this invention will become apparent to those skilled in the art. This invention is not to be duly limited to the illustrative embodiments set forth herein.

What is claimed is:

1. A method for reducing drying time of hair, the method comprising the steps of:
   (1) applying to hair that is wet or damp an aerosol hair drying aid composition that includes a propellant portion and a liquid portion, the liquid portion comprising:
      (a) at least one starch absorbent;
      (b) at least one modified clay mineral dispersing agent;
      (c) at least one hair conditioning agent selected from the group consisting of diisopropyl adipate, PPG-3 benzyl ether myristate, polyquaternium-59, butylene glycol, hydrolyzed pea protein PG-propyl silantriol, and combinations thereof;
      (d) at least one non-aqueous silicon-containing solvent; and
      (e) at least one non-aqueous $C_{1-9}$ mono alcohol solvent; and
   (2) allowing the hair to dry, wherein the hair is at least 70% dry after about 10 minutes.

2. The method of claim 1, wherein the absorbent is selected from the group consisting of corn starch, potato starch, tapioca starch, rice starch, wheat starch and cassava starch, and combinations thereof.

3. The method of claim 1, wherein the amount of total absorbent is from about 0.1 wt. % to about 75 wt. %, based upon the total weight of the liquid portion.

4. The method of claim 1, wherein the dispersing agent is disteardimonium hectorite.

5. The method of claim 1, wherein the amount of dispersing agent is from about 0.05 to about 12 wt. %, based upon the total weight of the liquid portion.

6. The method of claim 1, wherein the amount of total hair conditioning agent is from about 0.01 to about 25 wt. %, based upon the total weight of the liquid portion.

7. The method of claim 1, wherein the total amount of non-aqueous solvent is from about 20 to about 90 wt. %, based upon the total weight of the liquid portion.

8. The method of claim 1, wherein the liquid portion further comprises at least one anti-caking agent.

9. The method of claim 1, wherein the liquid portion further comprises at least one warming agent.

* * * * *